(12) United States Patent
Bergeron

(10) Patent No.: US 6,521,652 B1
(45) Date of Patent: *Feb. 18, 2003

(54) THIAZOLINE ACID DERIVATIVES

(75) Inventor: Raymond J. Bergeron, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/531,754

(22) Filed: Mar. 20, 2000

Related U.S. Application Data

(63) Continuation of application No. 09/144,103, filed on Aug. 31, 1998, now Pat. No. 6,083,966.

(51) Int. Cl.[7] ........................................... A61K 31/426
(52) U.S. Cl. ..................................................... 514/365
(58) Field of Search ........................... 548/201; 514/365

(56) References Cited

U.S. PATENT DOCUMENTS

| | | | |
|---|---|---|---|
| 3,809,754 A | 5/1974 | Bertrand | 424/270 |
| 3,882,110 A | 5/1975 | Clemence et al. | 260/247.1 |
| 4,367,233 A | 1/1983 | Clark et al. | 424/270 |
| 4,406,905 A | 9/1983 | Zähner et al. | 424/263 |
| 4,457,936 A * | 7/1984 | Draeger | 548/201 |
| 5,840,739 A | 11/1998 | Bergeron, Jr. | 514/365 |
| 6,083,966 A * | 7/2000 | Bergeron | 514/365 |

FOREIGN PATENT DOCUMENTS

| | | |
|---|---|---|
| DE | 2245 560 | 3/1974 |
| DE | 30 02 989 | 7/1981 |
| FR | 2 247 243 | 5/1975 |
| GB | 1292 170 | 10/1972 |
| GB | 1382 887 | 2/1975 |
| WO | WO94/11367 | 5/1994 |
| WO | WO97/36885 | 10/1997 |

OTHER PUBLICATIONS

Bergeron, R.J., et al. "Evaluation of Desferrithiocin and its Synthetic Analogues as Orally Effective Iron Chalators", *Journal of Medicinal Chemistry*, (1991), 34(7), 2072–2078.

Bergeron, R.J., et al. "Effects of C–4 Stereochemistry and C–4 Hydroxylation on the Iron Clearing Efficiency and Toxicity of Desferrithiocin Analogues", *Journal of Medicinal Chemistry*, (1999), 42(13), 2432–2440.

Jala, M.A.F., et al. "Structure of Anguibactin, a Unique Plasmid–Related Bacterial Siderophore from the Fish Pathogen Vibrio Anguillarum", *Journal of American Chemical Society*, (1989), 111(1), 292–296.

Ganguly, P.K., and Gupta, B.M., "Antiviral Activity of Isoquinolines Carbazoles and Other Miscellaneous Synthetic Chemicals in Mice," *Indian J. Med. Res.*, 63(10):1418–1426 (1975).

Raymond, K.N., and Carrano, C. J., "Coordination Chemistry and Microbial Iron Transport," *Acc. Chem. Res.*, 12:183–190 (1979).

Bergeron, R.J., "Iron: A Controlling Nutrient in Proliferative Processes," *Trends in Biochem. Sci.*, 11:133–136 (1986).

Finch, C.A. and Huebers, H.A., "Iron Metabolism," *Clin. Physiol. Biochem.*, 4:5–10 (1986).

Hallberg, L., "Bioavailability of Dietary Iron in Man," *Ann. Rev. Nutri.*, 1:123–147 (1981).

Finch, C.A., and Huebers, H., "Perspectives in Iron Metabolism," *N. Engl. J. Med.*, 306:1520–1528 (1982).

Finch, C.A., et al., "Ferrokinetics in Man," *Medicine (Baltimore)*, 49:17–53 (1970).

(List continued on next page.)

*Primary Examiner*—Robert Gerstl
(74) *Attorney, Agent, or Firm*—Hamilton, Brook, Smith & Reynolds, P.C.

(57) ABSTRACT

Phenyl- and pyridyl-substituted thiazoline acid derivatives useful in diagnosing and treating pathological conditions associated with an excess of trivalent metals in humans and animals.

52 Claims, 1 Drawing Sheet

Scheme: Synthesis of 4,5-Dihydro-2-(2,4-dihydroxy-R)-thiazole-4(S)-carboxylic acid Z = CH, R = Phenyl
Z = N, R = Pyridyl

OTHER PUBLICATIONS

Seligman, P.A., et al., "Molecular Mechanisms of Iron Metabolism," *The Molecular Basis of Blood Diseases*, p. 219–244 (1987).

O'Connell, M.J., et al., "The Role of Iron in Ferritin–and Haemosiderin–Mediated Lipid Peroxidation in Liposomes," *Biochem. J.*, 229:135–139 (1985).

Thomas, C.E., et al., "Ferritin and Superoxide–Dependent Lipid Peroxidation," *J. Biol. Chem.*, 260:3275–3280 (1985).

Weintraub, L.R., et al., "The Treatment of Hemochromatosis by Phlebotomy," *Med. Clin. N. Am.*, 50:1579–1590 (1966).

Hoffbrand, A.V., "Transfussion Sidersosis and Chelation Therapy," *Iron in Biochemistry and Medicine*, vol. II, p. 449, (London, 1980).

Brittenham, G.M., "Pyridoxal Isonicotinoyl Hydrazone: An Effective Iron–Chelator After Oral Administration," *Semin. Hematol.*, 27:112–116 (1990).

Bickel, V.H., et al., "Metabolic Properties of Actinomycetes. Ferrioxamine B," *Helv. Chim. Acta*, 43:2129–2138 (1960).

Ponka, P., et al., "Mobilization of Iron from Reticulocytes: Identification of Pyridoxal Isonicotinoyl Hydrazone as a New Iron Chelating Agent," *FEBS Lett.*, 97:317–321 (1979).

Uhlir, L.C., et al., "Specific Sequestering Agents for the Actinides. 21 Synthesis and Initial Biological Testing of Octadentate Mixed Catecholate–hydroxypyridinonate Ligands," *J. Med. Chem.*, 36:504–509 (1993).

Kontoghiorghes, et al., "1,2–Dimethyl–3–hydroxypyrid–4–one, an Orally Active Chelator for the Treatment of Iron Overload," *Lancet*, 1:1294–1295 (1987).

Grady, R.W., et al., "HBED: A Potential Oral Iron Chelator," *Ann. N.Y. Acad. Sci.*, 612:361–368 (1990).

Guterman, S.K., et al., "Feasibility of Enterochelin as an Iron–Chelating Drug: Studies with Human Serum and a Mouse Model System," *Gen. Pharmac.*, 9:123–127 (1978).

Grady, R.W., et al., "Rhodotorulic Acid–Investigation of its Potential as an Iron–Chelating Drug," *J. Pharmacol. Exp. Ther.*, 209:342–348 (1979).

Kishore, V., et al., "Synthesis of α–Poly–[$N^\epsilon$–(2–aryl–$\Delta^2$–thiazoline–4–carbonyl)–L–lysines] with Antiviral Activity," *Indian Journal of Chemistry*, 15B:255–257 (1977).

Bergeron, R.J., et al., "Synthesis and Biological Evaluation of Hydroxamate–Based Iron Chelators," *J. Med. Chem.*, 34:3182–3187 (1991).

Bergeron, R.J., et al., "A Comparison of the Iron–Clearing Properties of 1,2–Dimethyl–3–Hydroxypyrid–4–One 1,2–Diethyl–3–Hydroxypyrid–4–One and Deferoxamine," *Blood*, 79(7):1882–1890 (1992).

Bergeron, R.J., et al., "The Desferrithiocin Pharmacophore," *J. Med. Chem.*, 37:1411–1417 (1994).

Abstract for Accession No. 80:146142 from Chemical Abstract Database.

Abstract for Accession No. 83:206330 from Chemical Abstract Database.

\* cited by examiner

Scheme: Synthesis of 4,5-Dihydro-2-(2,4-dihydroxy-R)-thiazole-4(S)-carboxylic acid Z = CH, R = Phenyl
Z = N, R = Pyridyl

THIAZOLINE ACID DERIVATIVES

RELATED APPLICATIONS

This application is a continuation of U.S. Application No. 09/144,103 filed Aug. 31, 1998, now U.S. Pat. No. 6,083,966, the entire teachings of which are hereby incorporated by reference.

This application contains subject matter related to that disclosed and claimed in copending U.S. patent application Ser. No. 08/624,289 filed Mar. 29, 1996.

BACKGROUND OF THE INVENTION

Research leading to the completion of the invention was supported in part by Grant Nos. 3203522-12, RO1HL42817 and RO1DK49108 awarded by the National Institutes of Health (NIH). The United States Government has certain rights in and to the claimed invention.

1. Field of the Invention

The present invention relates to novel thiazoline acids and derivatives thereof useful as chelators of trivalent metals in therapeutic applications.

2. Discussion of the Prior Art

While many organisms are auxotrophic for Fe (III), because of the insolubility of the hydroxide ($K_{sp}=1\times10^{-38}$) [*Acc. Chem. Res.*, Vol. 12, Raymond et al, "Coordination Chemistry and Microbial Iron Transport," pages 183–190 (1979)] formed under physiological conditions, nature has developer rather sophisticated iron storage and transport systems. Microorganisms utilize low molecular weight ligands, siderophores, while eukaryotes tend to utilize proteins to transport iron, e.g., transferrin, and store iron, e.g., ferritin [*Trends in Biochem. Sci.*, Vol. 11, Bergeron, "Iron: A Controlling Nutrient in Proliferative Processes," pages 133–136 (1986)].

Iron metabolism in primates is characterized by a highly efficient recycling process with no specific mechanism for eliminating this transition metal [*Clin. Physiol. Biochem.*, Vol. 4, Finch et al, "Iron Metabolism," pages 5–10 (1986); *Ann. Rev. Nutri.*, Vol. 1, Hallberg, "Bioavailability of Dietary Iron in Man," pages 123–147 (1981); *N. Engl. J. Med.*, Vol. 306, Finch et al, "Perspectives in Iron Metabolism," pages 1520–1528 (1982); and *Medicine (Baltimore)*, Vol. 49, Finch et al, "Ferrokinetics in Man," pages 17–53 (1970)]. Because it cannot be effectively cleared, the introduction of "excess iron" into this closed metabolic loop leads to chronic overload and ultimately to peroxidative tissue damage [*The Molecular Basis of Blood Diseases*, Seligman et al, "Molecular Mechanisms of Iron Metabolism," page 219 (1987); *Biochem. J.*, Vol. 229, O'Connell et al, "The Role of Iron in Ferritin- and Haemosiderin-Mediated Lipid Peroxidation in Liposomes," pages 135–139 (1985); and *J. Biol. Chem.*, Vol. 260, Thomas et al "Ferritin and Superoxide-Dependent Lipid Peroxidation," pages 3275–3280 (1985)]. There are a number of scenarios which can account for "iron overload," e.g., high-iron diet, acute iron ingestion or malabsorption of the metal. In each of these situations, the patient can be treated by phlebotomy [*Med. Clin. N. Am.*, Vol. 50, Weintraub et al, "The Treatment of Hemochromatosis by Phlebotomy," pages 1579–1590 (1966)]. However, there are iron-overload syndromes secondary to chronic transfusion therapy, e.g., aplastic anemia and thalassemia, in which phlebotomy is not an option [*Iron in Biochemistry and Medicine*, Vol. II, Hoffbrand, "Transfusion Siderosis and Chelation Therapy," page 499 (London, 1980)]. The patient cannot be bled, as the origin of the excess iron is the transfused red blood cells; thus, the only alternative is chelation therapy. However, to be therapeutically effective, a chelator must be able to remove a minimum of between 0.25 and 0.40 mg of Fe/kg per day [*Semin. Hematol.*, Vol. 27, Brittenham, "Pyridoxal Isonicotinoyl Hydrazone: An Effective Iron-Chelator After Oral Administration," pages 112–116 (1990)].

Although considerable effort has been invested in the development of new therapeutics for managing thalassemia, the subcutaneous (sc) infusion of desferrioxamine B, a hexa coordinate hydroxamate iron chelator produced by *Streptomyces pilosus* [*Helv. Chim. Acta*, Vol. 43, Bickel et al, "Metabolic Properties of Actinomycetes. Ferrioxamine B," pages 2129–2138 (1960)], is still the protocol of choice. Although the drug's efficacy and long-term tolerability are well-documented, it suffers from a number of shortcomings associated with low efficiency and marginal oral activity.

Although a substantial number of synthetic iron chelators have been studied in recent years as potential orally active therapeutics, e.g., pyridoxyl isonicotinoyl hydrazone (PIH) [*FEBS Lett.*, Vol. 97, Ponka et al, "Mobilization of Iron from Reticulocytes: Identification of Pyridoxal Isonicotinoyl Hydrazone as a New Iron Chelating Agent," pages 317–321 (1979)], hydroxypyridones [*J. Med. Chem.*, Vol. 36, Uhlir et al, "Specific Sequestering Agents for the Actinides. 21. Synthesis and Initial Biological Testing of Octadentate Mixed Catecholate-hydroxypyridinonate Ligands," pages 504–509 (1993); and *Lancet*, Vol. 1, Kontoghiorghes et al, "1,2-Dimethyl-3-hydroxypyrid-4-one, an Orally Active Chelator for the Treatment of Iron Overload," pages 1294–1295 (1987)] and bis(o-hydroxybenzyl)-ethylenediaminediacetic acid (HBED; analogues [*Ann. N.Y. Acad. Sci.*, Vol. 612, Grady et al, "HBED: A Potential Oral Iron Chelator," pages 361–368 (1990)], none has yet proven to be completely satisfactory. Interestingly, the siderophores have remained relatively untouched in this search. Their evaluation as iron-clearing agents has not at all paralleled the rate of their isolation and structural elucidation. In fact, until recently, beyond DFO, only two or some 100 siderophores identified have been studied in animal models: enterobactin [*Gen. Pharmac.*, Vol. 9, Guterman et al, "Feasibility of Enterochelin as an Iron-Chelating Drug: Studies with Human Serum and a Mouse Model System," pages 123–127 (1978)] and rhodotorulic acid [*J. Pharmacol. Exp. Ther.*, Vol. 209, Grady et al, "Rhodotorulic Acid-Investigation of its Potential as an Iron-Chelating Drug," pages 342–348 (1979)]. While the former was only marginally effective at clearing iron, the latter compound was reasonably active. Unfortunately, both of these cyclic siderophores exhibited unacceptable toxicity, and neither possessed any oral activity. They were abandoned as there were any number of synthetic chelators with equally unsatisfactory properties from which to choose.

U.S. patent application Ser. No. 08/624,289 filed Mar. 29, 1996, the entire contents and disclosure of which are incorporated herein by reference, discloses certain 2-pyridyl-$\Delta^2$-thiazoline-4-carboxylic acids and derivatives thereof useful for the treatment of human and non-human animals in need of therapy entailing the prevention of deposition of trivalent metals and compounds thereof in their tissues, as well as the elimination of such metals and compounds from biological systems overloaded therewith.

It is an object of the present invention to provide additional novel thiazoline acids and derivatives thereof which, because of different volumes of distribution in patients and different lipophilicities than the derivatives of the prior art, provide the ability to control the pharmaco-kinetic properties and toxicities of the drugs.

Another object of the present invention is to provide novel pharmaceutical compositions for and methods of treatment of human and non-human animals in need of therapy entailing the prevention of deposition of trivalent metals and compounds thereof in tissues thereof, as well as the elimination of such metals and compounds from systems overloaded therewith.

SUMMARY OF THE INVENTION

The above and other objects are realized by the present invention, one embodiment of which comprises compounds of the formula:

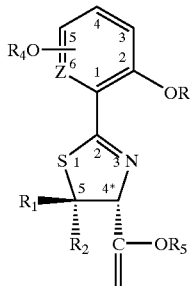

wherein: Z is CH or N;

R is H or acyl;

$R_1$, $R_2$, $R_3$ and $R_5$ may be the same or different and represent H, alkyl or hydrocarbyl arylalkyl having up to 14 carbon atoms; and $R_4$ is H or alkyl having 1–4 carbon atoms;

a salt thereof with a pharmaceutically acceptable acid or a pharmaceutically acceptable complex thereof.

Another embodiment of the invention relates to pharmaceutical compositions in unit dosage form comprising a therapeutically effective amount of the above compound and a pharmaceutically acceptable carrier therefor.

An additional embodiment of the invention concern methods of preventing or treating a pathological condition in a human or non-human animal that is associated with an excess of a trivalent metal, ion or compound thereof comprising administering to the animal a therapeutically effective amount of the compound defined above.

DETAILED DESCRIPTION OF THE INVENTION

Figure 1:
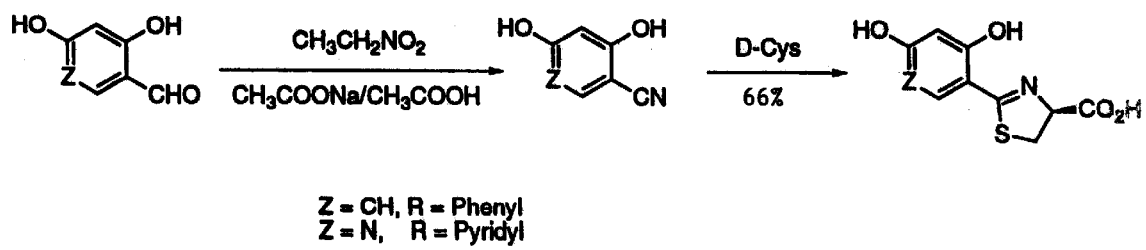
FIG. 1 depicts a reaction scheme for preparing the compounds of the invention.

The present invention is predicated on the discovery that compounds of the above formula are valuable bioactive chelators or sequestrants for trivalent metals such as Fe, Al and Cr. They can be administered to human and non-human mammals to prevent the deposition of, e.g., iron, in the tissues thereof. They are also useful for the elimination of, e.g., iron, from such mammals afflicted with, e.g., haemochromatosis, haemosiderosis and also cirrhosis. They also find application in dialysis, encephalopathy, osteomalacia and Alzheimer's disease.

The compounds described above are characterized by the asymmetric carbon atom marked with an asterisk (☆). The bonds surrounding these carbon atoms are arranged tetrahedrally and the substituents thus bonded to the asymmetric carbon atoms are in fixed positions. The formula represents optical antipodes exhibiting either the (S) or (R) conformation as shown in (i) and (ii) below:

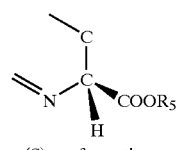

(S) conformation

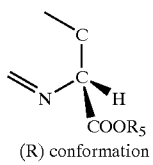

(R) conformation

In the above formula, R is preferably H, but may also be a suitable acyl group which is cleavable under physiological conditions to the free hydroxyl compounds and a biologically acceptable acid. Such acyl groups are known in the art, e.g., the acyl radical of a carbonic acid semiester, in particular carbonic acid semi-$C_1$–$C_4$-alkyl ester or carbonic acid semi-oxaalkyl ester in which oxaalkyl has 4–13 chain members such as an acyl radical —C(=O)—(O—CH$_2$—CH$_2$)$_n$—O-Alk in which n is an integer from 0 to 4 and Alk represents $C_1$–$C_4$ alkyl, in particular methyl or ethyl. Such acyl groups are, for example, methoxycarbonyl, ethoxycarbonyl or 2-(methoxyethoxy)-ethoxycarbonyl. Further acyl radicals are, for example, $C_1$–$C_3$-alkanoyl such as acetyl or propionyl, or mono-substituted or di-substituted carbamoyl such as di-$C_1$–$C_4$-alkyl carbamoyl, for example, dimethylcarbamoyl or diethylcarbamoyl, or $C_1$–$C_4$-alkoxycarbonyl-$C_1$–$C_4$-alkylcarbamoyl, for example, methoxycarbonylmethylcarbamoyl, ethoxycarbonylmethylcarbamoyl or 2-ethoxycarbonylethylcarbamoyl.

$R_1$, $R_2$, $R_3$ and $R_5$ may be the same or different and may be H, straight or branched chain alkyl having up to 14 carbon atoms, e.g., methyl, ethyl, propyl and butyl or arylalkyl wherein the aryl portion is hydrocarbyl and the alkyl portion is straight or branched chain, the arylalkyl group having up to 14 carbon atoms.

$R_4$ is H or straight or branched chain alkyl having 1 to 4 carbon atoms, e.g., methyl, ethyl, n-propyl, isopropyl, n-butyl, isobutyl, t-butyl.

Preferred among compounds of the above formula are those of the formula:

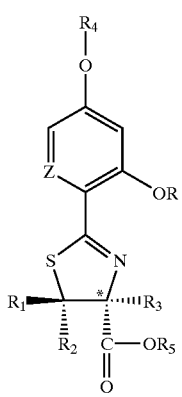

wherein: Z, R, $R_1$, $R_2$, $R_3$, $R_4$ and $R_5$ have the meanings ascribed above, as well as salts thereof with pharmaceutically acceptable acids and pharmaceutically acceptable complexes thereof.

Particularly preferred are those compounds of the above formula wherein:

a. Z is CH and $R=R_1=R_2R_3=R_4=R_5=H$;
b. Z is N and $R=R_1=R_2=R_3=R_4=R_5H$;

and most preferably, the optically pure isomers thereof.

It will be understood that salts of the compounds of the above formula with pharmaceutically acceptable acids also comprise part of the present invention. Suitable such acids include hydrochloric, sulfuric or phosphoric acids, as well as methanesulfonic, arginine, lysine, and the like.

The invention also includes pharmaceutically acceptable salts of the carboxylic acids of the above formula. Thus, ammonium salts and metal salts such as the alkali metal and alkaline earth metals salts, e.g., sodium, potassium, magnesium or calcium salts, as well as divalent metal salts such as zinc, and salts with suitable organic amines, there coming into consideration such salt formation especially aliphatic, cycloaliphatic, cycloaliphatic-aliphatic or araliphatic primary, secondary or tertiary mono-, di- or poly-amines, and also heterocyclic bases. Such amines are, for example, lower alkylamines, for example, triethylamine, hydroxy-lower alkylamines, for example, 2-hydroxyethylamine, bis-(2-hydroxyethyl)-amine or tris-(2-hydroxyethyl)-amine, basic aliphatic esters of carboxylic acids, for example, 4-aminobenzoic acid 2-diethylaminoethyl ester, lower alkyleneamines, for example, 1-ethylpiperidine, cycloalkylamines, for example, dicyclohexylamine, or benzylamines, for example, N,N'-dibenzylethylenediamine, also bases of the pyridine type, for example, pyridine, collidine or quinoline. Further salts include internal salts (zwitterionic forms of compounds of the invention), wherein a basic group, for example, the basic nitrogen atom present in the pyridine ring, is protonated by a hydrogen ion originating from an acid group in the molecule.

Owing to their high solubility and good tolerability, metal ion complexes of compounds of the above formulae, especially with suitable paramagnetic and/or radioactive metals, can be used as contrast agents in diagnostic medicine, for example, X-ray, radionuclide, ultrasound and/or magnetic resonance diagnostics.

Compounds of the above formulae may be synthesized according to the reaction scheme set forth in FIG. 1 wherein D-cys is D-cysteine or a reactive functional derivative thereof.

Free hydroxy groups present in the compounds of the above formulae are optionally protected by conventional protecting groups. Such protecting groups protect the hydroxy groups from undesired condensation reactions, substitution reactions and the like. The protecting groups can be introduced and removed easily, i.e., without undesirable secondary reactions taking place, for example, by solvolysis or reduction, in a manner known per se. Protecting groups and the methods by which they are introduced and split off are described, for example, in "Protective Groups in Organic Chemistry," Plenum Press, London, New York (1973) and also in "Methoden der organischen Chemie," Houben-Weyl, 4th edition, Vol. 15/1, Georg Thieme Verlag, Stuttgart (1974).

Suitable hydroxy-protecting groups are, for example, acyl radicals such as lower alkanoyl optionally substituted, for example, by halogen such as 2,2-dichloroacetyl, or acyl radicals of carbonic acid semiesters, especially tert.-butoxy-carbonyl, optionally substituted benzyloxycarbonyl, for example, 4-nitrobenzyloxycarbonyl, or diphenylmethoxycarbonyl, alkenyloxycarbonyl, for example, allyloxycarbonyl, or 2-halo-lower alkoxycarbonyl such as 2,2,2-trichloroethoxycarbonyl also trityl or formyl, or organic silyl radicals, also etherifying groups that can readily be split off such as tert.-lower alkyl, for example, tert.-butyl, or 2-oxa- or 2-thia-cycloalkyl having 5 or 6 ring atoms, for example tetrahydrofuryl or 2-tetrahydropyranyl or corresponding thia analogues, and also optionally substituted 1-phenyl-lower alkyl such as optionally substituted benzyl or diphenylmethyl, there coming into consideration as substituents of the phenyl radicals, for example, halogen such as chlorine, lower alkoxy such as methoxy, and/or nitro.

A reactive functional derivative of a carboxy group (Y) is, for example, an acid anhydride, an activated ester or an activated amide, cyano, a group of the formula —$C(OR_a)_3$ or —$C(=NH)$—$R_a$ in which $R_a$ is lower alkyl. Corresponding derivatives are well known in the art.

Of the anhydrides, the mixed anhydrides are especially suitable. Mixed anhydrides are, for example, those with inorganic acids such as hydrohalic acids, i.e., the corresponding acid halides, for example, chlorides or bromides, also with hydrazoic acid, i.e., the corresponding acid azides. Further mixed anhydrides are, for example, those with organic carboxylic acids such as with lower alkanecarboxylic acids optionally substituted, for example, by halogen such as fluorine or chlorine, for example, pivalic acid or trichloroacetic acid, or with semiesters, especially lower alkyl semiesters of carbonic acid such as the ethyl or isobutyl semiester of carbonic acid, or with organic, especially aliphatic or aromatic, sulfonic acids, for example, p-toluenesulfonic acid. Of the activated esters, there may be mentioned, for example, esters with vinylogous alcohols (i.e., enols such as vinylogous lower alkenols), or iminomethyl ester halides such as dimethyliminomethyl ester chloride (prepared from the carboxylic acid and, for example, dimethyl-(1-chloroethylidine)-iminium chloride of the formula $(CH_3)_2N^{\oplus}=C(Cl)CH_3Cl^{\ominus}$, which can be obtained, for example, from N,N-dimethylacetamide and phosgene), or aryl esters such as preferably suitable substituted phenyl esters, for example, phenyl ester substituted by halogen such as chlorine, and/or by nitro, for example, 4-nitrophenyl ester, 2,3-dinitrophenyl ester or 2,3,4,5,6-pentachlorophenyl ester, N-hetero-aromatic esters such as N-benztriazole esters, for example, 1-benztriazole ester, or N-diacylimino esters such as N-succinylamino or N-phthalylimino ester. Suitable activated amides are, for example, imidazolides, also 1,2,4-triazolides, tetrazolides or 1,2,4-oxadiazolinonides.

A preferred form of this process according to the invention is the reaction of a compound of the nitrile with a cysteine derivative. The reaction is carried out in an inert solvent such as an aqueous solvent at ambient temperature or, preferably, at slightly elevated temperature, for example, at about 50° to 80° C., and preferably under an inert gas atmosphere.

In resulting compounds in which one or more functional (hydroxy) groups are protected, the latter can be freed, optionally in stages or simultaneously, in a manner known per se, by means of solvolysis, especially hydrolysis or acidolysis, or in some cases also by means of careful reduction. Silyl protecting groups are advantageously split off with fluorides, for example, tetraethylammonium fluoride.

Salts of compounds of the invention can be manufactured in a manner known per se. Thus, salts of compounds having acidic groups can be formed, for example, by treating with metal compounds such as alkali metal salts of suitable organic carboxylic acids, for example, the sodium salt of α-ethylcaproic acid, or with inorganic alkali metal or alkaline earth metal salts, for example, sodium bicarbonate, or with ammonia or a suitable organic amine, preferably stoichiometric quantities or only a small excess of the salt-forming agent being used. Acid addition salts of compounds of the invention are obtained in a customary manner, for example, by treating with an acid or a suitable anion-exchange reagent. Internal salts of compounds of the invention (zwitterionic forms) can be formed, for example, by neutralizing the compounds or salts such as acid addition salts, to the isoelectric point, for example, with weak bases, or by treating with liquid ion exchangers.

Salts can be converted in a customary manner into the free compounds: metal and ammonium salts can be converted into the free compounds, for example, by treating with suitable acids, and acid addition salts, for example, by treating with a suitable basic agent.

The starting materials are available commercially and/or known or can be manufactured by known processes.

The racemate can be split in a manner known per se, for example, after conversion of the optical antipodes into diastereoisomers, for example, by reaction with optically active acids or bases.

The pharmacologically acceptable compounds of the present invention can be used, for example, for the manufacture of pharmaceutical compositions which contain an effective amount of the active substance together or in admixture with inorganic or organic, solid or liquid, pharmaceutically acceptable carriers.

The pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. The dosage of the active substance depends on the species of warm-blooded animal and on the age and individual condition, the illness to be treated and also on the mode of administration.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragees, tablets, capsules, suppositories or ampoules, and contain from approximately 0.05 g to approximately 10.0 g, and preferably from approximately 0.3 g to approximately 1.0 g, of the active ingredient.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragée cores In so doing, they can also be incorporated into plastics carriers which release the active substances or allow them to diffuse in controlled amounts.

Suitable carriers are especially fillers such as guars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragée cores are provided with suitable coatings that are, if desired, resistant to gastric juice, there being used, inter alia, concentrated sugar solutions which optionally contain gum arabic talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigment, can be added to the tablets or dragée coatings, for example for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for examples syrups prepared in a customary manner that contain the active ingredient in, for example, suspended form and in a concentration of approximately from 5% to 20%, and preferably approximately 10%, or in a similar concentration that provides a suitable single dose when administered, for example, in measures of 5 or 10 ml. Also suitable are, for example, powdered or liquid concentrates for preparing shakes, for example, in milk. Such concentrates can also be packed in single-dose quantities.

Particularly suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention also relates to compositions for diagnostic purposes that contain a suitable metal complex of a compound of the formula wherein Z, R, $R_1$, $R_2$, $R_3$, $R_4$ and $R_5$ are as previously defined.

The invention also relates to a method of treatment of pathological conditions in a mammal, especially human, which as has been described hereinabove, are associated with an excess of a trivalent metal cation such as aluminum or, especially, iron (III), in the body, which method comprises administering, preferably orally, a prophylactically or therapeutically effective amount of a compound of the formula or of a pharmaceutically acceptable salt thereof. There are used for this purpose especially the above-mentioned pharmaceutical compositions, a daily dose of from approximately 50 mg to approximately 10,000 mg, and preferably from approximately 300 mg to approximately 1,000 mg, of a compound of the present invention being administered to a warm-blooded animal of approximately 70 kg body weight. The dosage can be administered orally in several, for example, three, individual doses. For systemic, e.g., subcutaneous, administration, the more water-soluble salt forms of the compounds of the formula, e.g., the sodium salt, are preferred, for example, orally, or alternatively, subcutaneously.

The following examples serve to illustrate the invention, but should not be construed as a limitation thereof. Temperatures are given in degrees Centigrade.

Preparation of Drugs. Drug solutions were prepared in 60% water, 40% Cremophor RH-40.

EXAMPLE 1

2,4-Dihydroxybenzonitrile was prepared according to the method of Marcus in *Ber. dtsch. chem. Ges.* 1981, 24, 3651, as follows:

A mixture of 2,4-dihydroxybenzaldehyde (5.0 g, 36.4 mmol), sodium acetate (5.94 g, 72.4 mmol), nitroethane (5.44 g, 72.4 mmol) and glacial acetic acid (10 ml) was refluxed for 6 hours. After cooling, the mixture was poured onto ice (100 g) and extracted with ethyl acetate (4×50 ml). The combined organic layers were washed with saturated $NaHCO_3$ until the pH of the aqueous layer remained at 8, dried ($Na_2SO_4$) and the solvent removed in vacuo. Flash chromatography ($SiO_2$, cyclohexane:ethyl acetate=1:1) afforded 2,4-dihydroxybenzonitrile (2.87 g, 59%) as a pale yellow solid. $^1$H NMR (300 MHz, DMSO-$d_6$) δ 6.33 (d, 1H, J=8.6 Hz), 6.43 (s, 1H), 7.37 (d, 1H, J=8.6 Hz), 10.35 (s, 1H), 10.78 (s, 1H). IB (KBr) 2200 cm$^{-1}$.

EXAMPLE 2

4,5-Dihydro-2-(2,4-dihydroxyphenyl)-thiazole-4(S)-carboxylic acid was prepared as follows:

D-cysteine hydrochloride monohydrate (6.8 g, 38.7 mmol) was added to a solution of 2,4-dihydroxybenzonitrile (3.5 g, 25.9 mmol) prepared in Example 1, in a mixture of degassed methanol (105 ml) and 0.1 M phosphate buffer, pH 5.95 (70 ml). $NaHCO_3$ (3.25 g, 38.7 mmol) was carefully added and the mixture was stirred at 70° C. under Ar for 54 hours. Volatile components were removed under reduced pressure and the solution was acidified with 1 N HCl to pH 2. The resulting brown precipitate was vacuum filtered and the solid was washed with water (40 ml) and ethanol (20 ml). The crude product was dissolved in saturated $NaHCO_3$ (700 ml) and the aqueous solution washed with ethyl acetate (2×200 ml). The aqueous layer was filtered through a fine frit and acidified with 1 M HCl to pH 2. The precipitated product was vacuum filtered. The aqueous layer was extracted with ethyl acetate (4×400 ml), the combined organic extracts were dried ($Na_2SO_4$) and the solvent was removed in vacuo. The remaining solid was combined with the precipitated product and dried under high vacuum at 40° C. for 12 hours to give 4,5-dihydro-2-(2,4-dihydroxyphenyl)-thiazole-4(S)-carboxylic acid (4.08 g, 66%), mp 266–268° C. (dec) [*Ind. J. Chem.*, Vol. 15B, Kishore et al, pages 255–257 (1977) for (L)-isomer: 261–262° C.]. $^1$H NMR (300 MHz, DMSO-$d_6$) δ 3.61 (m, 2H), 5.38 (dd, 1H, J=7.2/9.4 Hz), 6.31 (d, 1H, J=2.3 Hz), 6.38 (dd, 1H, J=2.3/8.6 Hz), 7.25 (d, 1H, J=8.6 Hz), 10.25 (br s, 1H), 12.60 (br s, 1H), 13.15 (br s, 1H). Anal. calc. for $C_{10}H_9NO_4S$: C 50.20, N 3.79; N 5.85. Found: C 50.13, H 3.82, N 5.85.

Compounds of the invention in the scheme of FIG. 1 wherein Z is N may be prepared as described above in Examples 1 and 2 substituting the corresponding pyridyl aldehyde for 2,4-dihydroxybenzaldehyde.

The biological activity and properties of the compounds of the invention were evaluated as follows employing 4,5-dihydro-2-(2,4-dihydroxyphenyl)-thiazole-4(S)-carboxylic acid (1).

EXAMPLE 3

In Rats

Initial testing of 1 was performed in the non-iron-overloaded, bile duct-cannulated rat [*J. Med. Chem.*, Vol. 34, Bergeron et al, "Synthesis and Biological Evaluation of Hydroxamate-Based Iron Chelators," pages 3182–3187 (1991)]. The drug was prepared as a solution in 40% Cremophor-$H_2O$ and administered at a dose of 150 μmol/kg p.o. The rats were fasted for 24 hours before dosing. The efficiency of iron excretion induced by 1 was 2.4±0.92%.

EXAMPLE 4

In Monkeys

Given the results in the rat model, the ability of 1 to promote iron excretion in the iron-overloaded primate model [*Blood*, Vol. 79, Bergeron et al, "A Comparison of the Iron-Clearing Properties of 1,2-Dimethyl-3-Hydroxypyrid-4-One 1,2-Diethyl-3-Hydroxypyrid-4-one and Deferoxamine," pages 1882–1890 (1992)] was evaluated. The drug was prepared as a solution in 40% Cremophor-$H_2O$ and administered at a dose of 150 μmol/kg p.o. The monkeys were fasted for 24 hours before dosing. Immediately prior to drug administration, the monkeys were sedated with ketamine (7–10 mg/kg. i.m.) and given scopolamine (0.04–0.07 mg/kg/ i.m. to prevent ketamine-related salivation and vomiting. At the dose of 150 μmol/kg, the efficiency of 1 was 4.2±1.4% (n=4).

I claim:

1. A method of treating a pathological condition responsive to chelation or sequestration of a trivalent metal in a mammal comprising administering to said mammal a therapeutically or prophylactically effective amount of a compound of the formula:

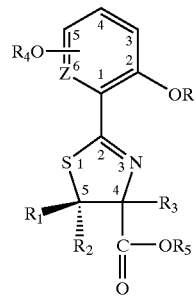

wherein:
  Z is CH or N;
  R is H or acyl;
  $R_1$, $R_2$, $R_3$ and $R_5$ may be the same or different and represent H, alkyl or hydrocarbyl arylalkyl having up to 14 carbons atoms;
  $R_4$ is H or alkyl having 1–4 carbon atoms;
and optical antipodes and mixtures thereof, diastereomers, racemates and salts thereof with a pharmaceutically acceptable acid or a pharmaceutically acceptable complex thereof.

2. The method of claim 1, wherein Z is CH.

3. The method of claim 2, wherein R=$R_1$=$R_2$=$R_3$=$R_4$=$R_5$=H.

4. The method of claim 1, wherein Z is N.

5. The method of claim 4 wherein R=$R_1$=$R_2$=$R_3$=$R_4$=$R_5$=H.

6. The method of claim 1, wherein Z is CH and $R_4$ is alkyl having 1–4 carbon atoms.

7. The method of claim 6, wherein R=$R_1$=$R_2$=$R_3$=$R_5$=H.

8. The method of claim 7, wherein $R_4$ is methyl.

9. The method of claim 1, wherein Z is N and $R_4$ is alkyl having 1–4 carbon atoms.

10. The method of claim 9, wherein R=$R_1$=$R_2$=$R_3$=$R_5$=H.

11. The method of claim 10, wherein $R_4$ is methyl.

12. The method of claim 1, wherein Z is CH and $R_1$ and $R_2$ are each alkyls having 1–4 carbon atoms.

13. The method of claim 12, wherein R=$R_3$=$R_4$=$R_5$=H.

14. The method of claim 13, wherein $R_1$ and $R_2$ are methyl.

15. The method of claim 1, wherein Z is CH and $R_3$ is an alkyl having 1–4 carbons atoms.

16. A method of claim 15, wherein R=$R_1$=$R_2$=$R_4$=$R_5$=H.

17. The method of claim 16, wherein $R_3$ is methyl.

18. The method of claim 1, wherein Z is CH and $R_1$, $R_2$ and $R_3$ are each alkyls having 1–4 carbons.

19. The method of claim 18, wherein R=$R_4$=$R_5$=H.

20. The method of claim 19, wherein $R_1$, $R_2$ and $R_3$ are methyl.

21. The method of claim 1, wherein the pathological condition is associated with the deposition of trivalent metal in the tissues of said patient.

22. The method of claim 1, wherein the pathological condition is associated with an excess of trivalent metal.

23. A method of treating a pathological condition responsive to chelation or sequestration of trivalent metal in a mammal in need thereof comprising administering to said mammal a therapeutically or prophylactically effective amount of a compound of the formula:

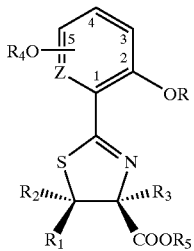

wherein:

Z is CH or N;

R is H or acyl;

$R_1$, $R_2$, $R_3$ and $R_5$ may be the same or different and represent H, alkyl or hydrocarbyl arylalkyl having up to 14 carbons atoms;

$R_4$ is H or alkyl having 1–4 carbon atoms;

optical antipodes and mixtures thereof, diastereomers, racemates and salts thereof with a pharmaceutically acceptable acid or a pharmaceutically acceptable complex thereof.

24. The method of claim 23, wherein Z is CH.

25. The method of claim 24, wherein R=$R_1$=$R_2$=$R_3$=$R_4$=$R_5$=H.

26. The method of claim 23, wherein Z is CH and $R_1$ and $R_2$ are alkyl having 1–4 carbons.

27. The method of claim 26, wherein R=$R_3$=$R_4$=$R_5$=H.

28. The method of claim 27, wherein $R_1$ and $R_2$ are methyl.

29. The method of claim 23, wherein Z is CH and $R_3$ is alkyl having 1–4 carbons.

30. The method of claim 29, wherein R=$R_1$=$R_2$=$R_4$=$R_5$=H.

31. The method of claim 30, wherein $R_3$ is methyl.

32. The method of claim 23, wherein Z is CH and $R_1$, $R_2$ and $R_3$ are alkyls having 1–4 carbons.

33. The method of claim 32, wherein R=$R_4$=$R_5$=H.

34. The method of claim 33, wherein $R_1$, $R_2$ and $R_3$ are methyl.

35. The method of claim 23, wherein the pathological condition is associated with the deposition of trivalent metal in the tissues of said patient.

36. The method of claim 23, wherein the pathological condition is associated with an excess of trivalent metal.

37. The method of claim 36, wherein the pathological condition is haemochromatosis, haemosiderosis or cirrhosis.

38. A method of treating a pathological condition responsive to chelation or sequestration of trivalent metal in a mammal in need thereof comprising administering to said mammal a therapeutically or prophylactically effective amount of a compound of the formula:

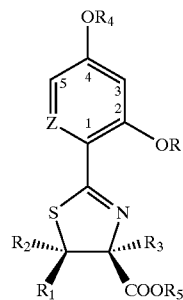

wherein:

Z is CH or N;

R is H or acyl;

$R_1$, $R_2$, $R_3$ and $R_5$ may be the same or different and represent H, alkyl or hydrocarbyl arylalkyl having up to 14 carbons atoms;

$R_4$ is H or alkyl having 1–4 carbon atoms;

optical antipodes and mixtures thereof, diastereomers, racemates and salts thereof with a pharmaceutically acceptable acid or a pharmaceutically acceptable complex thereof.

39. The method of claim 38, wherein Z is CH.

40. The method of claim 39, wherein R=$R_1$=$R_2$=$R_3$=$R_4$=$R_5$=H.

41. The method of claim 38, wherein Z is CH and $R_1$ and $R_2$ are alkyl having 1–4 carbons.

42. The method of claim 41, wherein R=$R_3$=$R_4$=$R_5$=H.

43. The method of claim 42, wherein $R_1$ and $R_2$ are methyl.

44. The method of claim 38, wherein Z is CH and $R_3$ is alkyl having 1–4 carbons.

45. The method of claim 44, wherein R=$R_1$=$R_2$=$R_4$=$R_5$=H.

46. The method of claim 45, wherein $R_3$ is methyl.

47. The method of claim 38, wherein Z is CH and $R_1$, $R_2$ and $R_3$ are alkyls having 1–4 carbons.

48. The method of claim 47, wherein R=$R_4$=$R_5$=H.

49. The method of claim 48, wherein $R_1$, $R_2$ and $R_3$ are methyl.

50. The method of claim 38, wherein the pathological condition is associated with the deposition of trivalent metal in the tissues of said patient.

51. The method of claim 38, wherein the pathological condition is associated with an excess of trivalent metal.

52. The method of claim 51, wherein the pathological condition is haemochromatosis, haemosiderosis or cirrhosis.

* * * * *

UNITED STATES PATENT AND TRADEMARK OFFICE
CERTIFICATE OF CORRECTION

PATENT NO.    : 6,521,652 B1
DATED         : February 18, 2003
INVENTOR(S)   : Raymond J. Bergeron, Jr.

It is certified that error appears in the above-identified patent and that said Letters Patent is hereby corrected as shown below:

Column 12,
Line 66, insert claim 53:
53. The method of Claim 22, wherein the pathological condition is haemochromatosis, haemosiderosis or cirrhosis.

Signed and Sealed this

Twelfth Day of August, 2003

JAMES E. ROGAN
*Director of the United States Patent and Trademark Office*